(12) United States Patent
Tsay et al.

(10) Patent No.: US 12,105,097 B2
(45) Date of Patent: Oct. 1, 2024

(54) RHEUMATOID ARTHRITIS AUTO-ANTIBODY-BOUND PEPTIDE AND APPLICATION THEREOF

(71) Applicant: China Medical University, Taichung (TW)

(72) Inventors: Gregory Tsay, Taichung (TW); Hsin-Yi Peng, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 584 days.

(21) Appl. No.: 17/269,257

(22) PCT Filed: Jan. 20, 2020

(86) PCT No.: PCT/CN2020/073097
§ 371 (c)(1),
(2) Date: Feb. 18, 2021

(87) PCT Pub. No.: WO2020/151631
PCT Pub. Date: Jul. 30, 2020

(65) Prior Publication Data
US 2021/0341491 A1    Nov. 4, 2021

Related U.S. Application Data

(60) Provisional application No. 62/797,351, filed on Jan. 27, 2019.

(51) Int. Cl.
*G01N 33/68* (2006.01)
*C07K 7/08* (2006.01)
*G01N 33/543* (2006.01)

(52) U.S. Cl.
CPC ........... *G01N 33/6893* (2013.01); *C07K 7/08* (2013.01); *G01N 33/54393* (2013.01); *G01N 2800/102* (2013.01)

(58) Field of Classification Search
None
See application file for complete search history.

(56) References Cited

U.S. PATENT DOCUMENTS

| | | | |
|---|---|---|---|
| 5,288,931 A * | 2/1994 | Chang | C07K 1/1133 530/825 |
| 7,112,660 B1 * | 9/2006 | Domingues | A61P 37/08 424/85.2 |
| 2003/0045474 A1 * | 3/2003 | Sailer | A61K 38/1875 514/8.8 |
| 2014/0154743 A1 * | 6/2014 | Levy | C07K 16/00 435/69.6 |

OTHER PUBLICATIONS

Tsay et al., 2017, J Immunol 198(1_Supplement):55.15, pp. 1-2.*
Triveri et al. (2021, J Chem Inf Model 61:4687-4700).*
Ulloa-Aguirre et al. (2004, Traffic 5:821-837).*
Bernier et al. (2004, Curr. Opin. Pharmacol. 4:528-533).*
Stobernack T. et al., Extracellular Proteome and Citrullinome of the Oral Pathogen Porphyromonas gingivalis J Proteome Res. Dec. 2, 2016;15(12):4532-4543.

* cited by examiner

*Primary Examiner* — Elizabeth C. Kemmerer
(74) *Attorney, Agent, or Firm* — Hannah Tien

(57) ABSTRACT

The present invention relates to a peptide capable of binding to rheumatoid arthritis autoantibodies, which is a consecutive 10-25 amino acid sequence of any one fragment of the group consisting of SEQ ID NO: 3-4, 7-13 or 16-19, wherein the peptide fragment has an epitope that binds to the rheumatoid arthritis autoantibodies. Furthermore, the peptide fragment bound to the rheumatoid arthritis autoantibodies is used for testing rheumatoid arthritis, and according to this use, the present invention provides a method for testing rheumatoid arthritis disease and a test reagent kit used for determining whether a subject to be tested suffers from rheumatoid arthritis disease.

9 Claims, 7 Drawing Sheets
Specification includes a Sequence Listing.

```
HA4: 1430-1703
NEAKVVLAADNVWGDNTGYQFLLDADHNTFGSVIPATGPLFTGTASSNLYSANFEYLIPANADPVVTTQN
IIVTGQGEVVIPGGVYDYCITNPEPASGKMWIAGDGGNQPARYDDFTFEAGKKYTFTMRRAGMGDGTDME
VEDDSPASYTYTVYRDGTKIKEGLTETTYRDAGMSAQSHEYCVEVKYAAGVSPKVCVDYIPDGVADVTAQ
KPYTLTVVGKTITVTCQGEAMIYDMNGRRLAAGRNTVVYTAQGGYYAVMVVVDGKSYVEKLAVK
```

RHEUMATOID ARTHRITIS AUTO-ANTIBODY-BOUND PEPTIDE AND APPLICATION THEREOF

CROSS-REFERENCES TO RELATED APPLICATIONS

This patent application is a U.S. National Stage Application of PCT/CN2020/073097 filed Jan. 20, 2020 and claims the benefit of priority from U.S. Provisional Application Ser. No. 62/797,351 filed Jan. 27, 2019, the contents of each of which is incorporated herein by reference in their entirety. This patent application also contains a Sequence Listing in a computer readable form, the file name is 3586-CMU-SEQ, created on Feb. 17, 2021, and the size is 8 KB, which is incorporated herein by reference. The Sequence Listing content of the PDF copy and the CRF copy (the ASCII file copy) are identical.

TECHNICAL FIELD

The present invention relates to a peptide fragment that binds to rheumatoid arthritis autoantibodies and its use for testing rheumatoid arthritis, according to this use, the present invention provides a method for testing rheumatoid arthritis disease and a test reagent kit used for determining whether a subject to be tested suffers from rheumatoid arthritis disease.

BACKGROUND OF THE INVENTION

Rheumatoid arthritis (RA) is a chronic inflammatory systemic autoimmune disease that affect approximately 0.5-1% of the world population, the prevalence rate in Taiwan is approximately 0.4%, and the ratio of male to female patients is approximately 1:3, the age of onset for 80% of the RA patients ranges from 35 to 50 years of age. At present, the cause of RA disease is yet unclear, recent studies indicate that it is primarily related to genes and environment (infection, smoking). Currently, with respect to the triggering mechanism of RA, the molecular mimicry hypothesis is the most widely accepted theory, that is, the patient has a specific gene, when an immune response is triggered by bacterial or viral infection, the immune response against the bacteria mistakenly identifies a body tissue as a foreign virus, and the body tissue (for example synovial tissue) is attacked, causing pathological changes.

Abnormal proliferation of synovial membrane and infiltration of T cells, B cells, macrophages and neutrophils are often seen in infected joints of RA patients. A Rheumatoid factor (RF) can be detected in the serum of approximately 70% of RA patients. RF is considered as one of the important factors that trigger the onset of RA, it can identify the constant region Fc region of human immunoglobulin G (IgG), and binds with this region to form an immune complex which in turn causes damages to the human body. Various autoantibodies can be found in RA patients, especially anti-citrullinated protein antibodies (ACPA), the sensitivity and specificity for diagnosing rheumatoid arthritis can be as high as approximately 70% and 90%, and the presence of antibodies can often be detected 7-10 years before the onset of rheumatoid arthritis, therefore they are currently used for diagnosing RA disease. In the initial onset of RA, swelling and pains in the small joints of fingers, feet or neck accompanied by morning stiffness for longer than 1 hour can usually be observed. If appropriate treatment is not provided, as the disease progresses the joints will gradually be damaged, deformed and lose athletic ability, leading to disability eventually. In addition to symptoms of arthritis, RA may also affect other organs such as lungs, skin, kidneys, or cause cardiovascular diseases.

Drugs used for RA treatment can be divided into three categories, non-steroidal anti-inflammatory drugs (NSAID), corticosteroid, and disease-modifying antirheumatic drugs (DMARD). Along with the development of biotechnology, there are more and more biologics and small molecule drugs, which are mainly used for inhibiting inflammation, including Etanercept, Infliximab, Adalimumab and Anakinra. Among them, Etanercept, Infliximab, and Adalimumab mainly inhibit immune responses triggered by TNF-α, interfere inflammatory reactions triggered by the binding of TNF in the joints of RA patients with cell surface receptors. Anakinra is an IL-1 receptor antagonist that can inhibit the effect of IL-1 in inflamed joints. In addition, there are other drugs under development, for example, anti-IL-6 and other anti-cytokine drugs or inhibitors such as Janus kinase-3 (JAK-3) inhibitor, spleen tyrosine kinase inhibitor, etc. that directly block inflammatory signals in the cells. Gradually, they are used in the treatment of RA to ameliorate the severity of the disease.

In addition to measurements of ACPA and RF in serum, the severity of the disease can also be evaluated through the disease activity score of 28 points (DAS28) index, erythrocyte sedimentation rate (ESR) and C-reactive protein (CRP), and treatment efficacy can be determined by observing whether the DAS 28 index decreases before and after medication. According to the new edition of ACR/EULAR 2010 rheumatoid arthritis classification criteria proposed by the American College of Rheumatology (ACR) and the European League Against Rheumatism (EULAR), with respect to rheumatoid arthritis, scores are obtained primarily by assessing joint involvement, acute phase reactants, serology and duration of symptoms, patients with a score higher than 6 are classified as having RA, the evaluation content is shown in Table 1.

TABLE 1

2010 Classification Criteria for Rheumatoid Arthritis
Target population (Who should be tested?): Patients have at least 1 joint with definite clinical synovitis (swelling) and with the synovitis not better explained by another disease.
Classification criteria for RA: In score of categories A-D, a patient having a cumulative score of 6 or higher is to be classified as having RA.

| Item | Score |
|---|---|
| A. Joint involvement | |
| 1 large joint | 0 |
| 2-10 large joints | 1 |
| 1-3 small joints (with or without involvement of large joints) | 2 |
| 4-10 small joints (with or without involvement of large joints) | 3 |
| >10 joints (at least 1 small joint) | 5 |
| B. Serology (at least 1 test result is needed for classification) | |
| Negative RF and negative ACPA | 0 |
| Between RF and ACPA at least one is higher than normal value, but lower than 3 times of the normal value | 2 |
| Between RF and ACPA at least one is higher than normal value, and higher than 3 times of the normal value | 3 |
| C. Acute-phase reactants (at least 1 test result is needed for classification) | |
| Normal CRP and normal ESR | 0 |
| CRP or ESR higher than normal value | 1 |

TABLE 1-continued

2010 Classification Criteria for Rheumatoid Arthritis
Target population (Who should be tested?): Patients have
at least 1 joint with definite clinical synovitis (swelling)
and with the synovitis not better explained by another disease.
Classification criteria for RA: In score of categories A-D, a patient
having a cumulative score of 6 or higher is to be classified as having RA.

| Item | Score |
|---|---|
| D. Duration of symptoms | |
| Shorter than 6 weeks | 0 |
| Longer than 6 weeks | 1 |

With respect to the serology in Table 1, currently the routine test includes RF (rheumatoid factor) and ACPA (Anti-citrullinated protein antibodies), since RF is found not only in patients with rheumatoid arthritis, the specificity is not very good, and the sensitivity and specificity of ACPA are higher than RF, as a result, the 2010 Classification Criteria for Rheumatoid Arthritis includes the test result of ACPA to be scored, the score is 2 either RF or ACPA is positive, the score is 3 when the value is higher than 3 times of the normal value.

Since rheumatoid arthritis cannot be prevented or cured, rheumatoid arthritis must be diagnosed early so that treatment can begin early for effective control. Clinically, rheumatoid arthritis is most likely to cause damages to the joints in the first two years of onset. The first two years of onset are the golden period for treatment, active treatment is required to maintain normal function of the joints and to reduce the chances of joint deformation. At present, with respect to RF or ACPA clinical tests, more than 30% of the patients are unable to obtain scores through serology. Therefore, it is necessary to develop more accurate serological tests in order to assist in the diagnosis of rheumatoid arthritis.

Rheumatoid arthritis (RA) and periodontal disease (PD) are closely related. The symptoms of these two are very similar, damages to joints or alveolar bone caused by chronic inflammation. Previous studies indicated that patients with rheumatoid arthritis suffered from periodontal disease were about two times higher than other people. Currently, pathogens related to infection of rheumatoid arthritis include Porphyromonas gingivalis (P. gingivalis), Epstein-Barr virus, Parvovl virus B19, etc. P. gingivalis is a gram-negative anaerobic, immobile, rod-shaped bacterium having a size of approximately 0.3-0.5 μm, and they form black colonies on a blood culture medium. P. gingivalis is also the main pathogen that causes periodontal disease at present, also the only bacterium known to produce peptidyl arginine deiminase (PAD). PAD is capable of modifying arginine in host proteins such as fibrinogen, α-enolase into citrulline, thereby causing this mechanism to be involved with the pathogenesis of rheumatoid arthritis.

P. gingivalis has many pathological factors, these factors can not only cause inflammation, but also help bacteria escape attacks of immune systems. One of the important pathological factors: Arg-gingipainA (RgpA) has been proven to be capable of decomposing its host's immunoglobulin, complements, and cytokines, and capable of increasing blood vessel permeability to enhance inflammatory responses. Studies in animal models indicated that when RpgA gene was deleted, the ability of P. gingivalis to infect its hosts would be suppressed. RgPA protein can be divided into three domains, Propeptide, catalytic domain and hemagglutinin. The propeptide is cleaved off during the process of protein maturation and is related to the transport of RgpA in bacteria; the catalytic domain has enzymatic activity and can cleave structures containing Arg-Xaa in the peptide; and the hemagglutinin domain can be divided into 4 sub-domains, and has hemagglutinating activity and participates in the binding and fixation of RgpA onto the outer membrane of the bacteria to help the bacteria approach red blood cells so as to obtain iron ions essential to their growth. ACPA can be used serologically as a component to diagnose rheumatoid arthritis. The mechanisms currently generated by ACPA may have three sources, in addition to genes and smoking, infection of P. gingivalis may also be one of the causes. Therefore, the present invention develops a novel peptide fragment through testing amino acid fragments in the RgpA protein of the periodontal pathogen P. gingivalis, and a use of the peptide fragment used for diagnosing rheumatoid arthritis, this novel serum test method can increase the sensitivity and specificity of diagnosis.

DETAILED DESCRIPTION OF THE INVENTION

The present invention relates to a peptide fragment that binds to rheumatoid arthritis autoantibodies and its use for testing rheumatoid arthritis. According to this use, the present invention provides a method for testing rheumatoid arthritis disease and a test reagent kit used for determining whether a subject to be tested suffers from rheumatoid arthritis disease.

According to one aspect of the present invention, a peptide capable of binding to rheumatoid arthritis autoantibodies is provided, a consecutive 10-25 amino acid sequence of any one fragment of the group consisting of SEQ ID NO. 3-4, 7-13 and 16-19, the peptide fragment has an epitope which binds to the rheumatoid arthritis autoantibodies. According to one embodiment of the present invention, the peptide fragment is composed of an amino acid sequence selected from the group consisting of SEQ ID NO: 8, 10, 11, 12, 17, 18 and 19. In another embodiment, the peptide fragment is composed of an amino acid sequence selected from the group consisting of SEQ ID NO: 11, 12, 17, 18, and 19. In another embodiment, the peptide fragment is composed of an amino acid sequence selected from the group consisting of SEQ ID NO: 12, 17, 18 or 19.

According to another aspect of the present invention, the present invention provides a method for testing rheumatoid arthritis, which comprises: testing the content of antibodies against the peptide of claim 1 in the blood of a subject to be tested; and comparing the content of the antibodies in a blood sample of the subject to be tested with the content of the same antibodies in a blood sample of a healthy subject, wherein when the content of the antibodies in the blood sample of the subject to be tested is 1.5 times of the content of the same antibodies in the blood sample of the healthy subject, the subject to be tested is likely to suffer from rheumatoid arthritis; and further giving the subject to be tested an effective amount of drugs for treating rheumatoid arthritis.

In another embodiment, wherein when the content of the antibodies in the blood sample of the subject to be tested is 2 times or more of the content of the same antibodies in the blood sample of the healthy subject, the subject to be tested is likely to suffer from rheumatoid arthritis.

In another embodiment, wherein when the content of the antibodies in the blood sample of the subject to be tested is 3 times or more of the content of the same antibodies in the blood sample of the healthy subject, the subject to be tested is likely to suffer from rheumatoid arthritis.

According to one embodiment of the present invention, wherein the testing method is an immunoassay method. In another embodiment, wherein the immunoassay method is selected from the group consisting of enzyme-linked immunosorbent assay, immunoblot analysis, immunoprecipitation analysis, radioimmunoassay, and immunochromatography analysis.

In one embodiment, wherein the immunoassay method can be combined with the principle of chromatography, in another embodiment, the peptide is immobilized on a nitrocellulose membrane, and after reaction color is developed with a coloring agent, colloidal gold particles, to test whether an antibody or an antigen to be tested is present in the sample to develop rapid test reagents. In one embodiment, the method for testing rheumatoid arthritis of the present invention can be further combined with diagnostic method for testing a rheumatoid factor (RF) and anti-citrullinated protein antibodies (ACPA).

According to another aspect of the present invention, the present invention hereby provides a reagent kit for testing rheumatoid arthritis, wherein the reagent kit comprises a peptide fragment that binds to rheumatoid arthritis autoantibodies, wherein the peptide fragment is composed of a consecutive amino acid sequence of any one fragment of the group consisting of SEQ ID NO: 3-4, 7-13 and 16-19, a solid support matrix bound to the peptide, and a secondary antibody having a probe label or unlabeled and capable of recognizing rheumatoid arthritis autoantibodies. In one embodiment, wherein the surface of the matrix in the reagent kit is coated with a protein crosslinking agent. In another embodiment, wherein the protein crosslinking agent is disuccinimidyl suberate (DDS). In another embodiment, wherein the matrix can be selected from the group consisting of ELISA plate, magnetic beads, polyvinylidene fluoride membrane (PVDF), agarose beads, polystyrene and Nitrocellulose membrane.

EXAMPLES

The samples used in the present invention were obtained from the China Medical University Hospital. Patients with rheumatoid arthritis were diagnosed by rheumatologists, appropriate classification criteria (ACR/EULAR 2010 rheumatoid arthritis classification criteria) were followed, reviewed and approved by the Human Research Ethics Committee of the China Medical University Hospital, and all participants consented to participate, and the samples were stored at −80° C. until analysis. The healthy subjects as defined in the present invention were individuals who did not suffer from rheumatoid arthritis.

Figure 1:
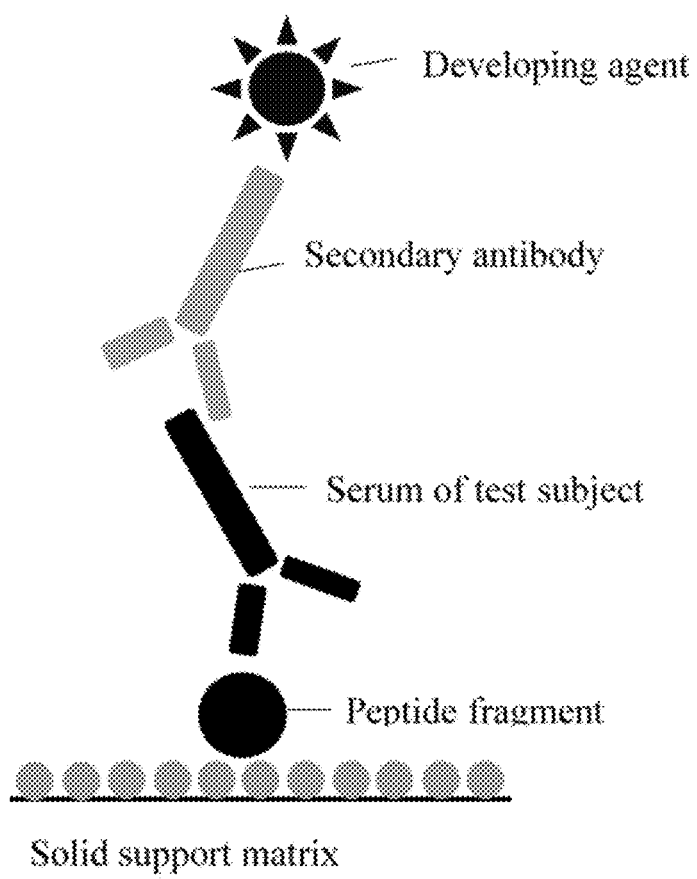
FIG. 1 is a schematic diagram illustrating the testing method of the present invention.

Enzyme-Linked Immunosorbent Assay (ELISA) was the principal experimental method for testing antigen-antibody binding, the main principle of the testing is shown in FIG. 1 and the main experimental procedure is described as follows:

Antigens of recombinant proteins or peptide fragments were diluted with a coating buffer, the diluted antigens were added with 5 ng of protein (100 μl/well) to the wells of a surface-pre-treated ELISA plate, and placed at 4° C. overnight for coating. The surface of the ELISA plate was first surface-treated with a protein crosslinking agent to increase the binding between the protein and the surface of the ELISA plate, then PBS solution (blocking buffer) containing 2% BSA was added and placed it at room temperature for one hour for non-specific blocking. The serum of a subject to be tested was diluted 100-fold with the blocking buffer, and added to the wells after being non-specifically blocked in duplicate and placed at 4° C. overnight for antigen-antibody binding. Then, after a washing step was repeated three times with a PBS solution (washing buffer) containing 0.1% Tween 20, secondary antibodies of the peroxidase-conjugated goat anti-human IgA or IgG diluted 2500 times with the blocking buffer were added for one hour of reaction at room temperature. After a washing step was repeated five times with the washing buffer, a developing agent containing ABTS peroxidase substrate solution was added, after 15 minutes of reaction, 5% of sodium dodecyl sulfate was added to terminate the reaction and read the absorbance value at OD405. Comparison was further conducted as the positive rate for testing RA diseases, wherein the criterion for the subjects to be tested to be determined as positive was three times of the average value of all healthy subjects, which was the critical point value (the value indicated by a dotted line in FIGS. 3-6).

Example 1

Figures 2A, 2B:
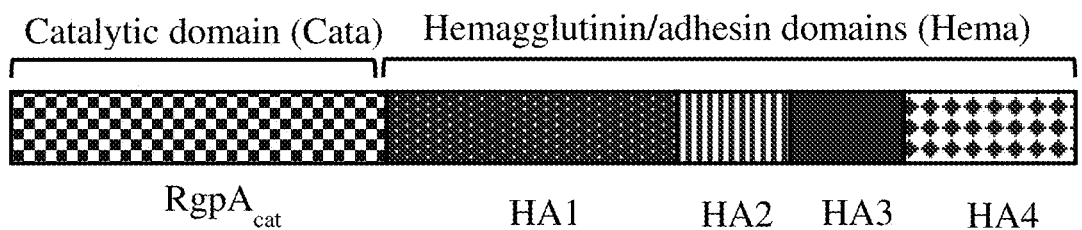
FIG. 2A is a schematic diagram of different functional domains of the RgpA protein of *Porphyromonas gingivalis*.
FIG. 2B is the amino acid sequence of the HA4 functional domain in the RgpA protein, and the HA4 sequence is used as a template to sequentially synthesize peptides p1-15. The underlined sequence regions are the overlapping sequence of each sequence.
Figure 3:
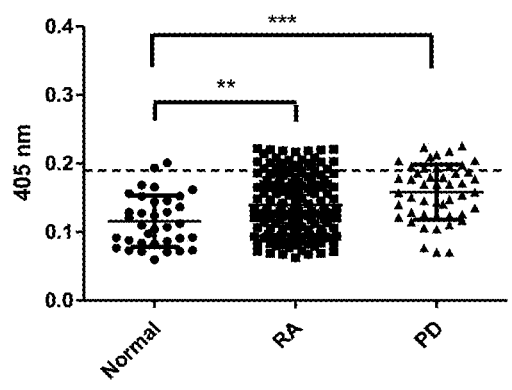
FIG. 3 is a diagram showing that the recombinant protein (Hema or Cata) of different protein functional domains of RgpA is used as an antigen to undergo immunological conjugation with the serum of a subject to be tested, and then IgG or IgA is respectively used as a secondary antibody for antigen-antibody response signal values, wherein (A) is anti-IgG-Hema, (B) is anti-IgA-Hema, (C) is anti-IgG-Cata, (D) is anti-IgA-Cata (Normal: healthy subjects, PD: patients with periodontal disease, RA: patients with rheumatoid arthritis).
Figure 3:
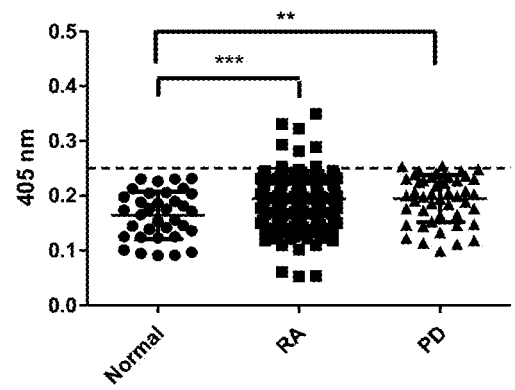
Figure 3:
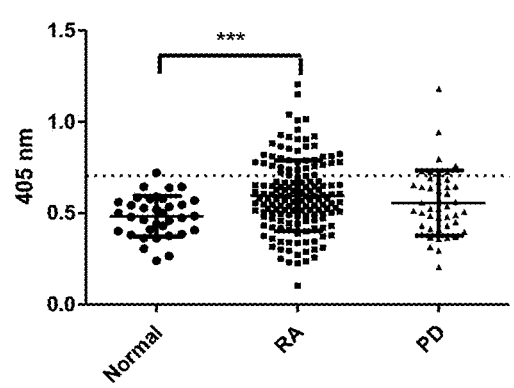
Figure 3:
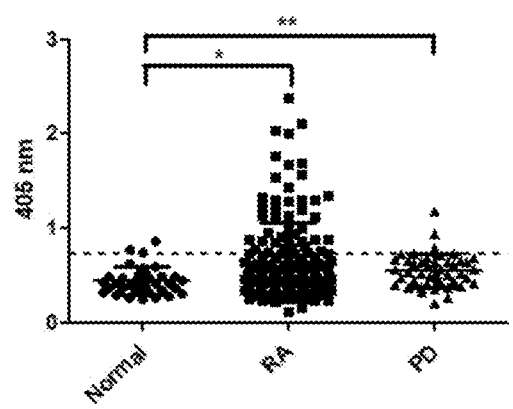
Figure 4:
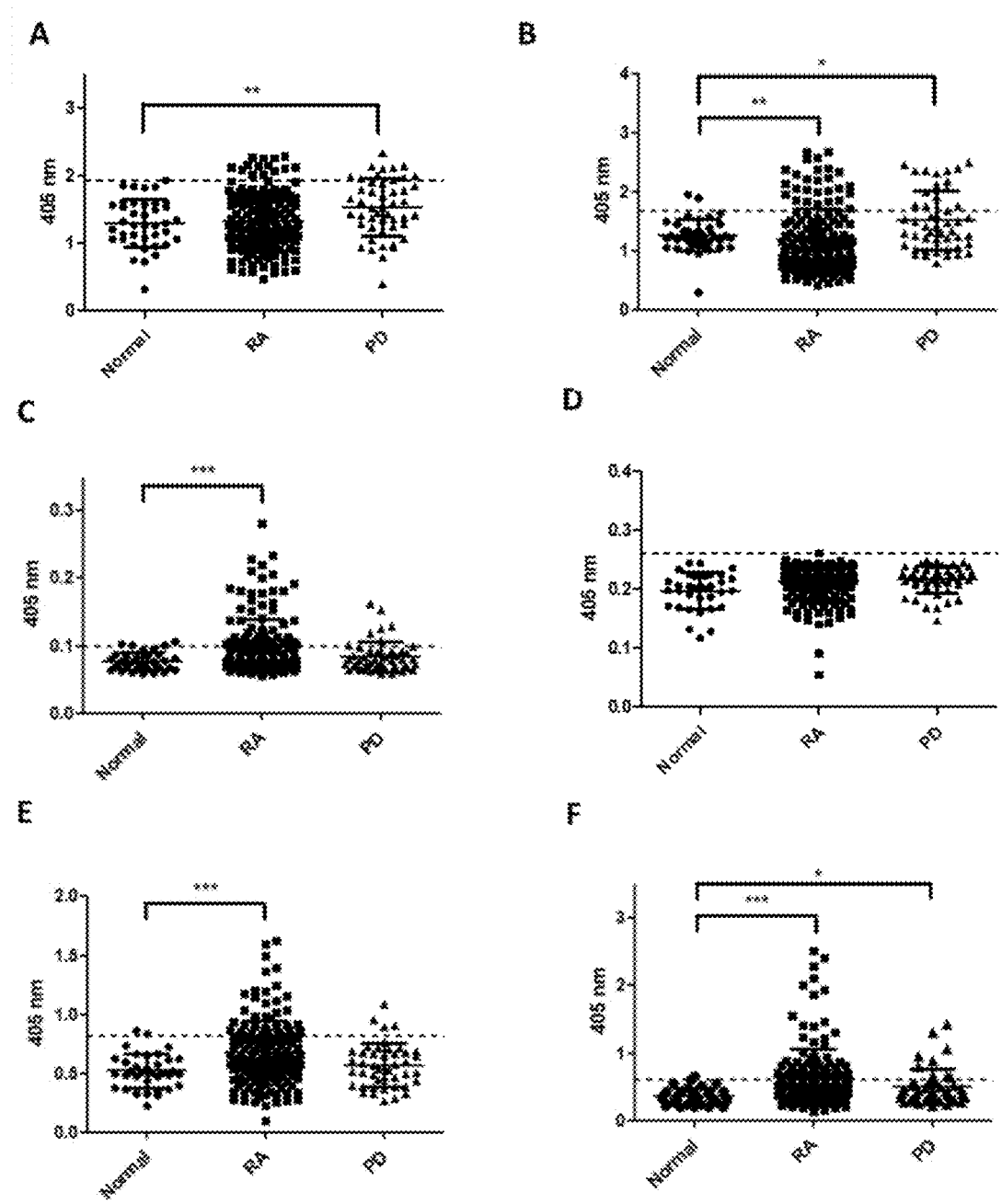
FIG. 4 is a diagram showing that the recombinant protein (HA1, HA2/3 or HA4) of different protein functional domains of RgpA is used as an antigen to undergo immunological conjugation with the serum of a subject to be tested, and then IgG or IgA is used as a secondary antibody for antigen-antibody response signal values, (A) is anti-IgG-HA1, (B) is anti-IgA-HA1, (C) is anti-IgG-HA2/3, (D) is anti-IgA-HA2/3, (E) is anti-IgG-HA4, (F) anti-IgA-HA4 (Normal: healthy subjects, PD: patients with periodontal disease, RA: patients with rheumatoid arthritis).

The functional domains of the RgpA protein of *Porphyromonas gingivalis* could be divided into: catalytic domain (Cata) and hemagglutinin domain (Hema), hemagglutinin domain was further divided into HA1, HA2/3 and HA4 (FIG. 2A), the gene fragments of the protein were cloned into a bacterial protein expression vector, then recombinant proteins were further expressed with an *E. coli* expression system, and an affinity column was used for recombinant proteins purification and proteins identification. Each of the purified protein fragments of *Porphyromonas gingivalis* RgpA was used as an antigen to test whether the serum of healthy subjects, RA patients and PD patients contained anti-RgpA-catalytic domain (Cata) and anti-RgpA-hemagglutinin domain (Hema) antibodies. The results in FIG. 3 show that anti-Hema antibodies (FIGS. 3A and 3B) and anti-RgpA-Cata antibodies (FIGS. 3C and 3D) could be detected in both RA and PD patients. The functional domains of Hema protein were further divided into HA1, HA2/3 and HA4 for testing. The results in FIG. 4 show that RA patients had higher anti-HA4 IgG antibodies (FIG. 4E) and IgA antibodies (FIG. 4F).

Example 2

The amino acid sequence of HA4 was further subjected to antigen epitope analysis. FIG. 2B shows the amino acid sequence of HA4, and the entire sequence was divided into 15 peptide fragments having overlapping sequences, further, the p10-p11 sequences were divided into 3 peptide fragments having overlapping sequences, their detailed sequences are shown in Table 2.

TABLE 2

The *Porphyromonas gingivalis* HA4 structural domain overlapping synthetic peptide list

| SEQ ID | Peptide Name | Amino Acid Sequence |
|---|---|---|
| NO: 2 | p1 | NEAKVVLAADNVWGDNTGYQFLLDA |
| NO: 3 | p2 | YQFLLDADHNTFGSVIPATGPLFTG |
| NO: 4 | p3 | TGPLFTGTASSNLYSANFEYLIPAN |
| NO: 5 | p4 | EYLIPANADPVVTTQNIIVTGQGEV |
| NO: 6 | p5 | VTGQGEVVIPGGVYDYCITNPEPAS |

TABLE 2-continued

The *Porphyromonas gingivalis* HA4 structural domain overlapping synthetic peptide list

| SEQ ID | Peptide Name | Amino Acid Sequence |
|---|---|---|
| NO: 7 | p6 | TNPEPASGKMWIAGDGGNQPARYDD |
| NO: 8 | p7 | QPARYDDFTFEAGKKYTFTMRRAGM |
| NO: 9 | p8 | TMRRAGMGDGTDMEVEDDSPASYTY |
| NO: 10 | p9 | SPASYTYTVYRDGTKIKEGLTETTY |
| NO: 11 | p10 | GLTETTYRDAGMSAQSHEYCVEVKY |
| NO: 12 | p11 | YCVEVKYAAGVSPKVCVDYIPDGVA |
| NO: 13 | p12 | YIPDGVADVTAQKPYTLTVVGKTIT |
| NO: 14 | p13 | VVGKTITVTCQGEAMIYDMNGRRLA |
| NO: 15 | p14 | MNGRRLAAGRNTVVYTAQGGYYAVM |
| NO: 16 | p15 | GGYYAVMVVVDGKSYVEKLAVK |

Figure 5:
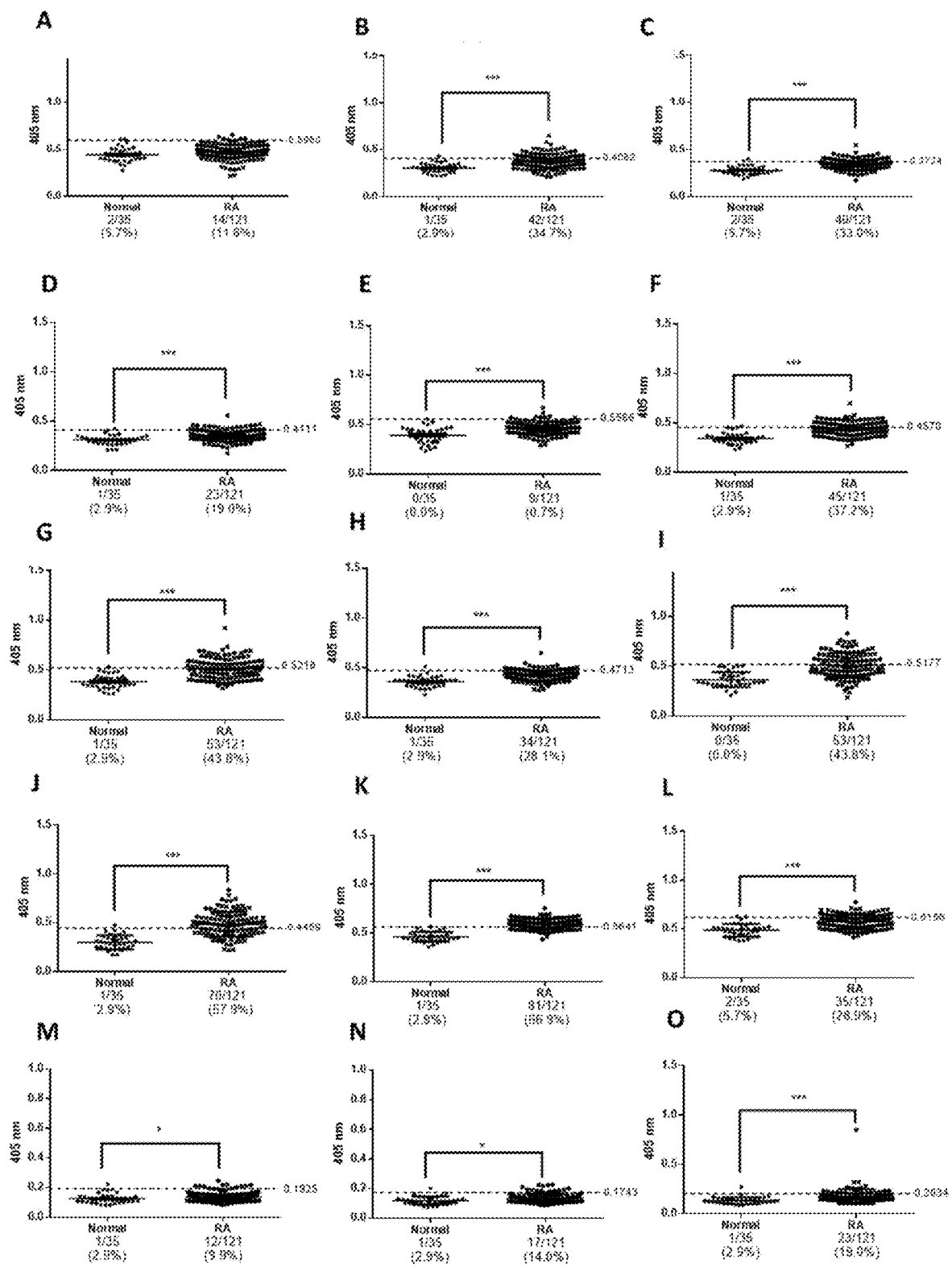
FIG. 5 is a diagram showing that a peptide fragment of the HA4 functional domain of RgpA protein is used as an antigen to undergo immunological conjugation with the serum of a subject to be tested, and then IgG is used as a secondary antibody for antigen-antibody response signal values, wherein (A) is the peptide sequence p1, (B) the peptide sequence p2, (C) the peptide sequence p3, (D) the peptide sequence p4, (E) the peptide sequence p5, (F) the peptide sequence p6, (G) the peptide sequence p7, (H) the peptide sequence p8, (I) the peptide sequence p9, (J) the peptide sequence p10, (K) the peptide sequence p11, (L) the peptide sequence p12, (M) the peptide sequence p13, (N) the peptide sequence p14, (O) the peptide sequence p15 (Normal: healthy subjects, RA: patients with rheumatoid arthritis).

Peptide fragments p1-p15 were used as antigens to test whether the serum of healthy subjects and RA patients contained antibodies against each peptide. The results in FIG. 5 show that compared to healthy subjects, the antibodies against the peptide contained in the serum of RA patients increased in varying degrees. Furthermore, the cutoff value (three times of the average value of the healthy subjects) was used to test the positive rate of RA disease (the value indicated by dotted lines in FIG. 5), the respective positive rate of the tests could be calculated (Table 3).

TABLE 3

Positive rate of healthy subjects and RA patients (Cohort 1) tested with Porphyromonas gingivalis HA4 domain overlapping synthetic peptide sequence 1-15

| Peptide Name | Healthy Subjects, n (%) n = 35 | RA Patients, n (%) n = 121 |
|---|---|---|
| p1 | 2 (5.7) | 14 (11.6 |
| p2 | 1 (2.9) | 42 (34.7) |
| p3 | 2 (5.7) | 40 (33.0) |
| p4 | 1 (2.9) | 23 (19.0) |
| p5 | 0 (0) | 9 (0.7) |
| p6 | 1 (2.9) | 45 (37.2) |
| p7 | 1 (2.9) | 53 (43.8) |
| p8 | 1 (2.9) | 34 (28.1) |
| p9 | 0 (0) | 53 (43.8) |
| p10 | 1 (2.9) | 70 (57.8) |
| p11 | 2 (5.7) | 79 (66.1) |
| p12 | 0 (0) | 35 (28.9) |
| p13 | 1 (2.9) | 12 (9.9) |
| p14 | 1 (2.9) | 17 (12.9) |
| p15 | 1 (2.9) | 31 (20.0) |

Example 3

With respect to the p10-p11 sequence in HA4, the consecutive sequence was cut into three peptide fragments having overlapping sequences and named as p11M1, p11M2 and p11M3. Their detailed sequences are shown in Table 4.

TABLE 4

Peptide fragments p10-p11 structural domain overlapping synthetic peptide in HA4

| SEQ ID | Peptide Name | Amino Acid Sequence |
|---|---|---|
| NO: 17 | p11M1 | AAGVSPKVCVDYIPDGVA |
| NO: 18 | p11M2 | AQSHEYCVEVKYAAGVSP |
| NO: 19 | p11M3 | GLTETTYRDAGMSAQSHE |

Figure 6:
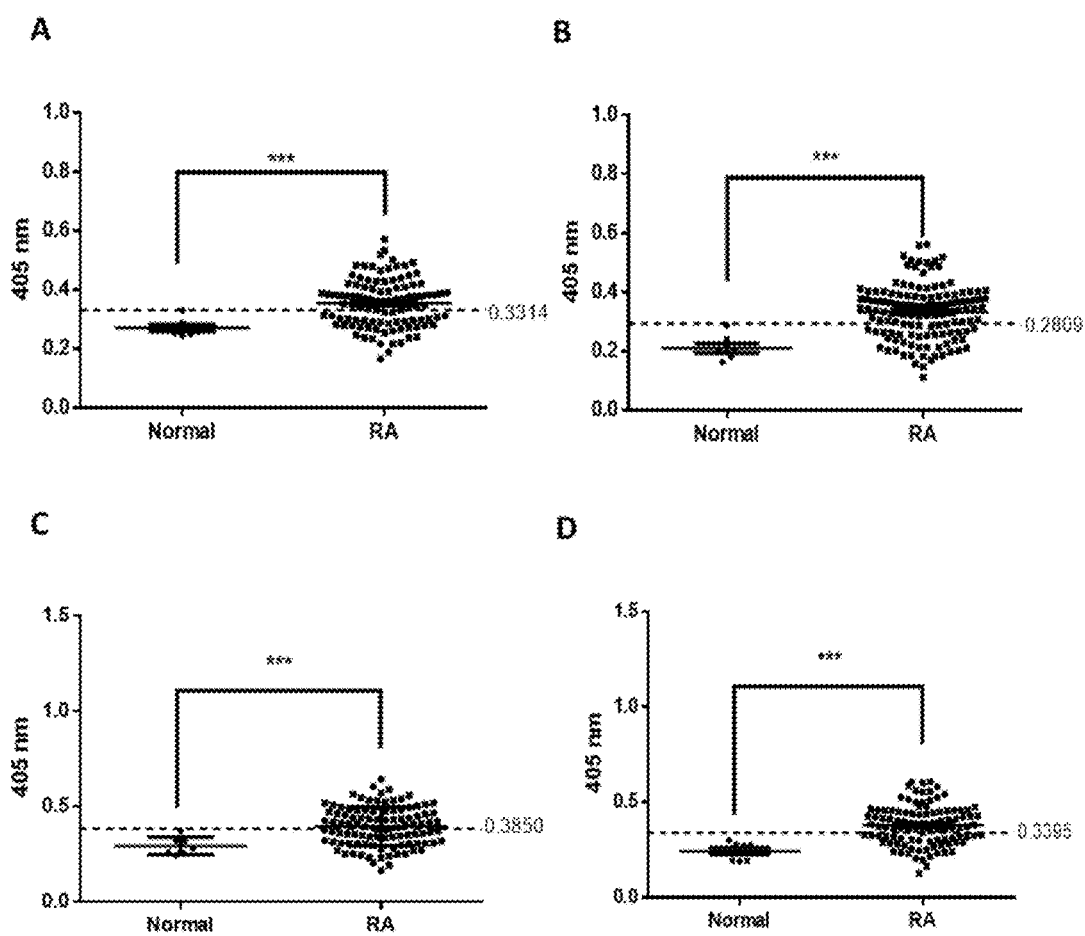
FIG. 6 is a diagram showing that the peptide fragment p11 or its derivative fragments of the HA4 functional domain of the RgpA protein is used as an antigen to undergo immunological conjugation with the serum of a subject to be tested, and then IgG is used as a secondary antibody for antigen-antibody response signal values, wherein (A) is the peptide sequence p11, (B) the peptide sequence p11M1, (C) the peptide sequence p11M2, (D) the peptide sequence p11M3 (Normal: healthy subjects, RA: patients with rheumatoid arthritis).

P11 and its peptide derivative fragments (p11M1, p11M2 and p11M3) were used as antigens to test whether antibodies against each peptide fragment were contained in the serum of healthy subjects and RA patients. The results in FIG. 6 show that, as compared to healthy subjects, antibodies against the peptide fragment p11 and its peptide derivatives could be significantly detected in the serum of the RA patients. Furthermore, the cutoff value (three times of the average value of the healthy subjects) was used to test the positive rate of RA diseases (the value indicated by dotted lines in FIG. 6), and the respective positive rate of the tests could be calculated (Table 5).

TABLE 5

Comparison of positive rates of peptide 11 and its peptide derivatives used for diagnosis of RA (Cohort 2)

| Peptide Name | Healthy Subject, n (%) n = 7 | RA Patients, n (%) n = 103 |
|---|---|---|
| p11 | 0 (0) | 61 (59.2) |
| p11M1 | 0 (0) | 65 (63.1) |
| p11M2 | 0 (0) | 53 (51.4) |
| p11M3 | 0 (0) | 63 (61.2) |

Further, the experimental data were used to establish a ROC curve, and to obtain AUC (area under the curve) values. The AUC value was often used to evaluate the diagnostic value of a test. The higher the value, the higher the diagnostic value was. Generally speaking, when the AUC was between 0.7 and 0.9, the test method was highly accurate. As shown in Table 6, the AUC values obtained by testing the antibodies against peptide fragment p11 and its peptide derivatives were all between 0.8 and 0.9.

TABLE 6

Comparison of the accuracy of peptide p11 and its peptide derivatives used for RA diagnosis (Cohort 2)

| Peptide Name | Sensitivity(%) | Specificity (%) | AUC |
|---|---|---|---|
| p11 | 59.8 | 100 | 0.8326 |
| p11M1 | 65.05 | 100 | 0.8969 |
| p11M2 | 57.84 | 100 | 0.7997 |
| p11M3 | 74.51 | 100 | 0.8973 |

In previous research reports, the serological test items were used to test the expression of RF and ACPA by using the enzyme-linked immunosorbent assay, the in vitro test reagent manufacturers included Menarini, Thermo Fisher, Inova, Roche, Abbott, and Euroimmun. In 2018, scholar Van Hoovels compared the positive rates of RF and ACPA tests available commercially: the positive rate of RF for serological diagnosis of patients with rheumatoid arthritis was 35-60%, and the positive rate of ACPA was 35-41%. The calculated AUC values for RF and ACPA were 0.68-0.71 and 0.67-0.77, respectively (Ann Rheum Dis. 2018, 77 (5): 667-67). Therefore, no matter the comparison was based on the positive rate of diagnosis or the AUC value, the method for diagnosing RA by testing the antibodies against peptide 11 and its peptide derivatives was more sensitive and more accurate than current tests of RF and ACPA.

Example 4

For 121 patients suffering from rheumatoid arthritis, commercially available test kits (brand: Inova) were used to test RF and ACPA. Based on the results shown in Table 8 the positive rate for RF was 44.6% and the positive rate for ACPA was 53.7%. The positive rate, when having both RF and ACPA, was 54.5%, therefore 45.5% of the patients showed double negatives with respect to RF and ACPA (RF/ACPA"), that is, RA disease could not be detected by current serological test methods. However, the present invention tested the antibodies against peptide 11 as a method for diagnosis of RA, its positive rate was 65.3%, and its sensitivity was higher than the value of RF or ACPA or a combination of both.

Further, 55 people (45.5%) having double negatives for RF and ACPA were tested with antibodies against peptide p11, the results showed that 31 of them were tested to be suffering from RA. Therefore, when the test results of the antibodies against peptide p11 were combined, the positive rate of RA by testing RF and ACPA could be increased to 80.2% (Table 7-9). Therefore, in the present invention, for those rheumatoid arthritis patients whose RF and ACPA test results were negative by using the currently commercially available test kits, the sensitivity of serological diagnosis could be improved to be more accurately, so that physicians could intervene earlier with treatment to relieve joint pains and inflammatory responses, and ameliorate the condition of bone erosion caused by rheumatoid arthritis.

TABLE 7

Comparison of the positive rates of RF, ACP and antibodies against peptide p11 used for testing RA patients (Cohort 1, n = 121)

| Test Target | Positive Rate, n (%) |
|---|---|
| RF⁺ | 44.6% |
| ACPA⁺ | 53.7% |
| RF⁺/ACPA⁺ | 66 (54.5%) |
| RF⁻/ACPA⁻ | 55 (45.5%) |
| Anti-p11⁺ | 65.3% |

TABLE 8

55 RF⁻/ACPA⁻ RA patients further tested with anti-peptide p11 antibody expression (Cohort 1, n = 55)

| Test Target | Positive Rate, n (%) |
|---|---|
| RF⁻/ACPA⁻/Anti-p11⁺ | 31 (56.4%) |
| RF⁻/ACPA⁻/Anti-p11⁻ | 24 (77.4%) |

TABLE 9

Predicted positive rate of combined RF, ACPA and anti-peptide p11 antibodies (Cohort 1, n = 121, RA patients)

| Test Target | Positive Rate, n (%) |
|---|---|
| RF+/ACPA+ | 66 (54.5%) |
| RF−/ACPA−/Anti-p11+ | 31 (56.4%) |
| RF+/ACPA+ combined with RF−/ACPA−/Anti-p11+ | 97 (80%) |

Example 5

Figure 7:
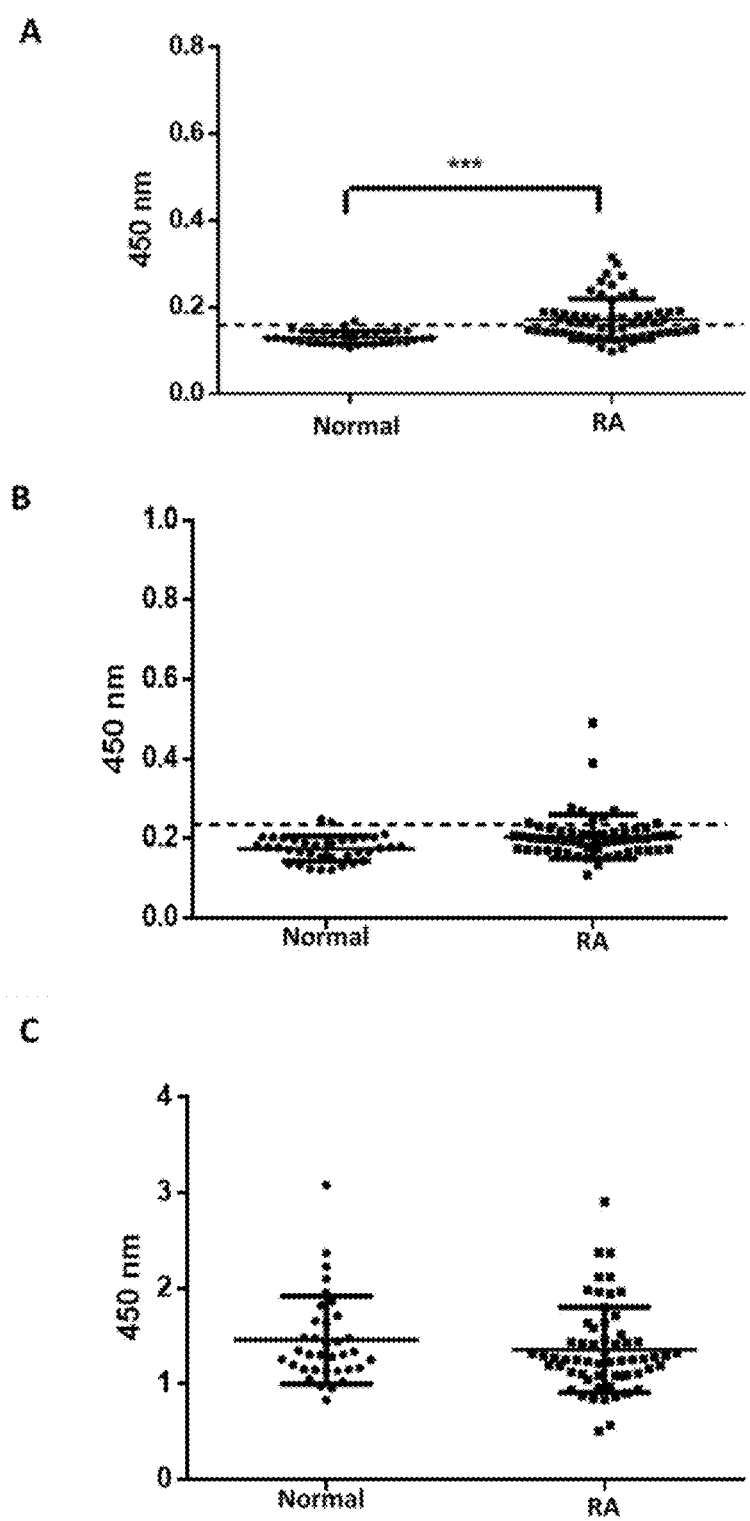
FIG. 7 shows the response of using different coating methods to detect the immunological conjugation of the peptide fragment p11 and the serum of a subject to be tested, wherein (A) the ELISA plate is treated with DSS, (B) the ELISA plate is not subjected to any treatment, (C) the commercially available DLISA plate having specially treated surface (mainly aimed at enhancing peptide conjugation).

Since the binding between the peptide fragment and the ELISA plate could be improved when the surface of the ELISA plate was treated, the accuracy of testing serum antibodies of RA patients could be increased. In this example, a protein crosslinking agent-disuccinimidyl suberate (DSS) was used for surface treatment, and commercially available ELISA plate capable of increasing peptide binding capacity was used for comparison and analysis, positive rates of RA diagnosis were obtained through testing anti-peptide p11 antibody in the serum of healthy subjects and RA patients, the test results were further determined based on the positive rates. FIG. 7 and Table 10 show that when DSS was used to treat the surface, the positive rate of RA patients could be increased (FIG. 7A shows the test using an ELISA plate not treated with DSS and FIG. 7B shows the test using an ELISA plate treated with DSS). On the other hand, though commercially available ELISA plates was able to improve the binding of peptides to ELISA plates, identifiable and specific epitopes could not be provided. The results in FIG. 7C show that the absorbance values were significantly improved with respect to the DDS-treated and untreated ELISA plates, but the specificity that can distinguish the antibodies in the serum of healthy subjects and RA patients was absent (FIG. 7C).

TABLE 10

Comparison of the positive rate of anti-peptide p11 antibodies with or without DSS coating for RA diagnosis (Cohort 2)

| | Healthy Subjects, n (%) n = 35 | RA Patients, n (%) n = 61 |
|---|---|---|
| ELISAPlate-no coating | 2 (5.7) | 9 (14.8%) |
| ELISA Plate-DSS coating | 1 (2.8) | 33 (54.1%) |

What is claimed is:

1. A peptide capable of binding to rheumatoid arthritis autoantibodies, which is composed of the amino acid sequence selected from the group consisting of SEQ ID NOs: 8, 10, 11, 12, 17, 18, and 19.

2. A method for testing rheumatoid arthritis, which comprises:
contacting a first blood sample of a subject to be tested with the peptide of claim 1 to allow for binding of the peptide to antibodies in the first blood sample;
contacting a second blood sample of a healthy subject with the peptide of claim 1 to allow for binding of the peptide to antibodies in the second blood sample;
comparing the amount of bound antibodies in the first blood sample of the subject to be tested with the amount of the same bound antibodies in the second blood sample of the heathy subject, wherein when the amount of the bound antibodies in the first blood sample of the subject to be tested is 1.5 times of the amount of the same bound antibodies in the second blood sample of the healthy subject, the subject to be tested is likely to suffer from rheumatoid arthritis.

3. The method of claim 2, wherein when the amount of the bound antibodies in the first blood sample of the subject to be tested is 3 times or more of the amount of the same bound antibodies in the second blood sample of the healthy subject, the subject to be tested is likely to suffer from rheumatoid arthritis.

4. The method of claim 2, wherein the method for assaying the amount of the bound antibodies is selected from the group consisting of enzyme-linked immunosorbent assay, immunoblot analysis, immunoprecipitation analysis, radioimmunoassay, and immunochromatography analysis.

5. The method of claim 4, which can be further combined with a diagnostic method for testing rheumatoid factor and anti-citrullinated protein antibodies.

6. A reagent kit for testing rheumatoid arthritis, which comprises the peptide of claim 1, a solid support matrix bound to the peptide, and a secondary antibody capable of binding rheumatoid arthritis autoantibodies, wherein the second antibody is labeled or unlabeled.

7. The reagent kit of claim 6, wherein the surface of the matrix in the reagent kit is coated with a protein crosslinking agent.

8. The reagent kit of claim 7, wherein the protein crosslinking agent is disuccinimidyl suberate.

9. The reagent kit of claim 6, wherein the matrix is selected from the group consisting of an ELISA plate, magnetic beads, polyvinylidene fluoride membrane, agarose beads, polystyrene and Nitrocellulose membrane.

* * * * *

SEQUENCE LISTING

<160> NUMBER OF SEQ ID NOS: 19

<210> SEQ ID NO 1
<211> LENGTH: 274
<212> TYPE: PRT
<213> ORGANISM: Porphyromonas gingivalis

<400> SEQUENCE: 1

Asn Glu Ala Lys Val Val Leu Ala Ala Asp Asn Val Trp Gly Asp Asn
1               5                   10                  15

Thr Gly Tyr Gln Phe Leu Leu Asp Ala Asp His Asn Thr Phe Gly Ser
            20                  25                  30

Val Ile Pro Ala Thr Gly Pro Leu Phe Thr Gly Thr Ala Ser Ser Asn
        35                  40                  45

Leu Tyr Ser Ala Asn Phe Glu Tyr Leu Ile Pro Ala Asn Ala Asp Pro
    50                  55                  60

Val Val Thr Thr Gln Asn Ile Ile Val Thr Gly Gln Gly Glu Val Val
65                  70                  75                  80

Ile Pro Gly Gly Val Tyr Asp Tyr Cys Ile Thr Asn Pro Glu Pro Ala
                85                  90                  95

Ser Gly Lys Met Trp Ile Ala Gly Asp Gly Gly Asn Gln Pro Ala Arg
            100                 105                 110

Tyr Asp Asp Phe Thr Phe Glu Ala Gly Lys Lys Tyr Thr Phe Thr Met
        115                 120                 125

Arg Arg Ala Gly Met Gly Asp Gly Thr Asp Met Glu Val Glu Asp Asp
    130                 135                 140

Ser Pro Ala Ser Tyr Thr Tyr Thr Val Tyr Arg Asp Gly Thr Lys Ile
145                 150                 155                 160

Lys Glu Gly Leu Thr Glu Thr Thr Tyr Arg Asp Ala Gly Met Ser Ala
                165                 170                 175

Gln Ser His Glu Tyr Cys Val Glu Val Lys Tyr Ala Ala Gly Val Ser
            180                 185                 190

Pro Lys Val Cys Val Asp Tyr Ile Pro Asp Gly Val Ala Asp Val Thr

```
                195                 200                 205
Ala Gln Lys Pro Tyr Thr Leu Thr Val Val Gly Lys Thr Ile Thr Val
        210                 215                 220

Thr Cys Gln Gly Glu Ala Met Ile Tyr Asp Met Asn Gly Arg Arg Leu
225                 230                 235                 240

Ala Ala Gly Arg Asn Thr Val Val Tyr Thr Ala Gln Gly Gly Tyr Tyr
                245                 250                 255

Ala Val Met Val Val Asp Gly Lys Ser Tyr Val Glu Lys Leu Ala
            260                 265                 270

Val Lys

<210> SEQ ID NO 2
<211> LENGTH: 25
<212> TYPE: PRT
<213> ORGANISM: Porphyromonas gingivalis

<400> SEQUENCE: 2

Asn Glu Ala Lys Val Val Leu Ala Ala Asp Asn Val Trp Gly Asp Asn
1               5                   10                  15

Thr Gly Tyr Gln Phe Leu Leu Asp Ala
            20                  25

<210> SEQ ID NO 3
<211> LENGTH: 25
<212> TYPE: PRT
<213> ORGANISM: Porphyromonas gingivalis

<400> SEQUENCE: 3

Tyr Gln Phe Leu Leu Asp Ala Asp His Asn Thr Phe Gly Ser Val Ile
1               5                   10                  15

Pro Ala Thr Gly Pro Leu Phe Thr Gly
            20                  25

<210> SEQ ID NO 4
<211> LENGTH: 25
<212> TYPE: PRT
<213> ORGANISM: Porphyromonas gingivalis

<400> SEQUENCE: 4

Thr Gly Pro Leu Phe Thr Gly Thr Ala Ser Ser Asn Leu Tyr Ser Ala
1               5                   10                  15

Asn Phe Glu Tyr Leu Ile Pro Ala Asn
            20                  25

<210> SEQ ID NO 5
<211> LENGTH: 25
<212> TYPE: PRT
<213> ORGANISM: Porphyromonas gingivalis

<400> SEQUENCE: 5

Glu Tyr Leu Ile Pro Ala Asn Ala Asp Pro Val Val Thr Gln Asn
1               5                   10                  15

Ile Ile Val Thr Gly Gln Gly Glu Val
            20                  25

<210> SEQ ID NO 6
<211> LENGTH: 25
<212> TYPE: PRT
<213> ORGANISM: Porphyromonas gingivalis

<400> SEQUENCE: 6
```

```
Val Thr Gly Gln Gly Glu Val Val Ile Pro Gly Gly Val Tyr Asp Tyr
1               5                   10                  15

Cys Ile Thr Asn Pro Glu Pro Ala Ser
            20                  25
```

<210> SEQ ID NO 7
<211> LENGTH: 25
<212> TYPE: PRT
<213> ORGANISM: Porphyromonas gingivalis

<400> SEQUENCE: 7

```
Thr Asn Pro Glu Pro Ala Ser Gly Lys Met Trp Ile Ala Gly Asp Gly
1               5                   10                  15

Gly Asn Gln Pro Ala Arg Tyr Asp Asp
            20                  25
```

<210> SEQ ID NO 8
<211> LENGTH: 25
<212> TYPE: PRT
<213> ORGANISM: Porphyromonas gingivalis

<400> SEQUENCE: 8

```
Gln Pro Ala Arg Tyr Asp Asp Phe Thr Phe Glu Ala Gly Lys Lys Tyr
1               5                   10                  15

Thr Phe Thr Met Arg Arg Ala Gly Met
            20                  25
```

<210> SEQ ID NO 9
<211> LENGTH: 25
<212> TYPE: PRT
<213> ORGANISM: Porphyromonas gingivalis

<400> SEQUENCE: 9

```
Thr Met Arg Arg Ala Gly Met Gly Asp Gly Thr Asp Met Glu Val Glu
1               5                   10                  15

Asp Asp Ser Pro Ala Ser Tyr Thr Tyr
            20                  25
```

<210> SEQ ID NO 10
<211> LENGTH: 25
<212> TYPE: PRT
<213> ORGANISM: Porphyromonas gingivalis

<400> SEQUENCE: 10

```
Ser Pro Ala Ser Tyr Thr Tyr Thr Val Tyr Arg Asp Gly Thr Lys Ile
1               5                   10                  15

Lys Glu Gly Leu Thr Glu Thr Thr Tyr
            20                  25
```

<210> SEQ ID NO 11
<211> LENGTH: 25
<212> TYPE: PRT
<213> ORGANISM: Porphyromonas gingivalis

<400> SEQUENCE: 11

```
Gly Leu Thr Glu Thr Thr Tyr Arg Asp Ala Gly Met Ser Ala Gln Ser
1               5                   10                  15

His Glu Tyr Cys Val Glu Val Lys Tyr
            20                  25
```

<210> SEQ ID NO 12

```
<211> LENGTH: 25
<212> TYPE: PRT
<213> ORGANISM: Porphyromonas gingivalis

<400> SEQUENCE: 12

Tyr Cys Val Glu Val Lys Tyr Ala Ala Gly Val Ser Pro Lys Val Cys
 1               5                  10                  15

Val Asp Tyr Ile Pro Asp Gly Val Ala
            20                  25

<210> SEQ ID NO 13
<211> LENGTH: 25
<212> TYPE: PRT
<213> ORGANISM: Porphyromonas gingivalis

<400> SEQUENCE: 13

Tyr Ile Pro Asp Gly Val Ala Asp Val Thr Ala Gln Lys Pro Tyr Thr
 1               5                  10                  15

Leu Thr Val Val Gly Lys Thr Ile Thr
            20                  25

<210> SEQ ID NO 14
<211> LENGTH: 25
<212> TYPE: PRT
<213> ORGANISM: Porphyromonas gingivalis

<400> SEQUENCE: 14

Val Val Gly Lys Thr Ile Thr Val Thr Cys Gln Gly Glu Ala Met Ile
 1               5                  10                  15

Tyr Asp Met Asn Gly Arg Arg Leu Ala
            20                  25

<210> SEQ ID NO 15
<211> LENGTH: 25
<212> TYPE: PRT
<213> ORGANISM: Porphyromonas gingivalis

<400> SEQUENCE: 15

Met Asn Gly Arg Arg Leu Ala Ala Gly Arg Asn Thr Val Val Tyr Thr
 1               5                  10                  15

Ala Gln Gly Gly Tyr Tyr Ala Val Met
            20                  25

<210> SEQ ID NO 16
<211> LENGTH: 22
<212> TYPE: PRT
<213> ORGANISM: Porphyromonas gingivalis

<400> SEQUENCE: 16

Gly Gly Tyr Tyr Ala Val Met Val Val Asp Gly Lys Ser Tyr Val
 1               5                  10                  15

Glu Lys Leu Ala Val Lys
            20

<210> SEQ ID NO 17
<211> LENGTH: 18
<212> TYPE: PRT
<213> ORGANISM: Porphyromonas gingivalis

<400> SEQUENCE: 17

Ala Ala Gly Val Ser Pro Lys Val Cys Val Asp Tyr Ile Pro Asp Gly
 1               5                  10                  15
```

```
Val Ala

<210> SEQ ID NO 18
<211> LENGTH: 18
<212> TYPE: PRT
<213> ORGANISM: Porphyromonas gingivalis

<400> SEQUENCE: 18

Ala Gln Ser His Glu Tyr Cys Val Glu Val Lys Tyr Ala Ala Gly Val
1               5                   10                  15

Ser Pro

<210> SEQ ID NO 19
<211> LENGTH: 18
<212> TYPE: PRT
<213> ORGANISM: Porphyromonas gingivalis

<400> SEQUENCE: 19

Gly Leu Thr Glu Thr Thr Tyr Arg Asp Ala Gly Met Ser Ala Gln Ser
1               5                   10                  15

His Glu
```